United States Patent [19]

Fleer

[11] 4,080,737

[45] Mar. 28, 1978

[54] COUPLING DEVICE FOR DENTAL HANDPIECES

[75] Inventor: Ernst Otto Fleer, Bensheim Auerbach, Germany

[73] Assignee: Siemens Aktiengesellschaft, Berlin & Munich, Germany

[21] Appl. No.: 732,405

[22] Filed: Oct. 14, 1976

[30] Foreign Application Priority Data

Nov. 3, 1975 Germany .............................. 2549177

[51] Int. Cl.² ............................................. A61C 19/02
[52] U.S. Cl. ........................................... 32/22; 32/27
[58] Field of Search .............................. 32/22, 23, 27; 128/24 A, 303 R, 303.1, 62 A, 172.1, 362; 339/15, 185, 16 R; 174/47

[56] References Cited

U.S. PATENT DOCUMENTS

| 3,809,977 | 5/1974 | Balamuth | 128/24 A |
| 3,992,565 | 11/1976 | Gatfield | 174/47 |

Primary Examiner—Robert Peshock
Attorney, Agent, or Firm—Hill, Gross, Simpson, Van Santen, Steadman, Chiara & Simpson

[57] ABSTRACT

A coupling device for detachably connecting a medical device, such as a dental handpiece, which requires at least one operating medium selected from a group consisting of electrical currents, propulsion gas, auxiliary gas, water and light and has a conduit for each of the required mediums, to a supply tube containing feed lines for at least one of the operating mediums characterized by the coupling device including a pair of coupling halves having coacting coupling links, and means for holding the coupling halves in coupling engagement. Each of the coacting coupling links is located in a specific spatial position in accordance with a pattern so that the coupling half attached to the supply tube can be utilized for coupling a different medical device which requires different selected operating mediums.

14 Claims, 5 Drawing Figures

COUPLING DEVICE FOR DENTAL HANDPIECES

BACKGROUND OF THE INVENTION

1. Field of the Invention

The present invention is directed to a coupling device for detachably connecting a medical device in particular dental handpieces to a supply tube which contains feed lines for at least one operating medium selected from electrical current, air, water and light with the coupling device comprising a pair of coupling halves which are either firmly or detachably connected respectively to the supply tube and the medical device and have sets of coupling links arranged to coact for transmission of the operating medium from the feed lines on the tube side to those on the handpiece or medical device side. The operating mediums may be of a general nature or of a specific nature such as for example a propulsion gas or air, a cooling air, spray air, spray water or electrical currents with varying or different rates of voltages.

2. Prior Art

Medical devices such as dental handpieces are of various constructions and types, for example turbine drill handpieces, micromotor handpieces, and spray handpieces. For example for a turbine handpiece, the operating medium is a driving or propulsion air and the handpiece is provided with auxiliary air and water for producing a spray mist which is often referred to as spray air and spray water. In addition, it is ofter desirable to provide illumination in the area of the drill or burr and the turbine handpiece will often include a light conductor which is connected to a light conductor in the supply tube for transmitting light to a desired position on the turbine handpiece. Handpieces, which have an electrical motor as a drive source, such as the micromotor handpieces, in addition to requiring electrical current for driving the micromotor will require cooling air for the motor. Frequently spray water is also supplied to the handpiece for spraying the area on which the drill or burr is operating.

Since each of these handpieces requires a different operating medium or a different combination of operating mediums, a coupling device for one type of handpiece, which device is used to connect the handpiece to a coupling hose, will have a different arrangement of coupling links with different dimensions than the coupling device for another type of handpiece. Since the different handpieces have different requirements for its operating medium, this different construction of the coupling links is understandable. However, if one produces six different types of handpieces, and each type of handpiece requires a different operating medium, coupling devices of six different constructions or types are necessary with one type associated with each of the six different types of handpieces.

To provide a coupling device that is designed for each of the different types of handpieces involves large expenses for designing the different types of coupling devices, for manufacturing the different types of coupling devices and for maintaining or keeping an inventory of each of the different types of coupling devices in stock. In addition, since the coupling device for a handpiece of one type may be slightly different for a coupling device of a different handpiece of the same type, the exchange of the two handpieces may require exchanging a portion of the coupling member or handpiece. Furthermore, since the supply tube for one type of handpiece only provides the operating mediums for the one type of handpiece, an exchange of the handpiece with a handpiece of a different type usually requires replacing the supply tube.

Insofar that each handpiece is usually constructed so that it is rotatable relative to the associated supply tube, the handpiece is usually equipped with a rotational coupling. This rotational coupling usually is of a different design for each type of handpiece. Frequently, a rotational coupling is also present in the handpiece in addition to the actual coupling of the handpiece to the tube. In the case of handpieces with electromotive drive such as the micromotor handpieces, a rotational coupling is arranged between the portion of the handpiece containing the drive motor and the actual grip portion. This provides a disadvantage in that each of the plurality of grip portions which may be used with one drive motor portion must be provided with the rotational coupling which increases the cost of the device.

SUMMARY OF THE INVENTION

The present invention is directed to the task of providing a simplification for a coupling device of the type which is used for coupling a medical device such as a dental handpiece with the supply tube. This simplification, which includes a standardization of the coupling device, reduces the cost for designing the coupling device, the cost of manufacturing of the coupling device and reduces the number of coupling devices which must be maintained in an inventory or stock. By standardizing the coupling device which is used with each of the different types of dental handpieces, it is possible to change the handpiece which is associated with one of the supply tubes so that a rarely used handpiece may be connected when necessary to a supply tube of a relatively frequently used handpiece whose supply tube is arranged at a particular readily accessible position on the dental apparatus.

To achieve these improvements, a coupling device for detachably connecting a medical device, in particular a dental handpiece, which medical device requires at least one operating medium selected from a group consisting of electrical currents, propulsion gas, auxiliary gas, water and light and has a conduit for each of the required mediums, to a supply tube containing feed lines for at least one of the operating mediums, said coupling device includes a pair of coupling halves with the first coupling half connected to the medical device and having first coupling links for each of the conduits and a second coupling half connected to the supply tube and having a second coupling link for each feed line, and means for interconnecting the pair of coupling halves with the first and second coupling links coacting to interconnect the feed line of the supply tube to the respective conduit of the medical device, the improvement comprises the first and second coupling links for each operating medium being provided on said first and second halves in a specific spatial position in accordance with a pattern so that the second coupling half can be selectively connected to a feed line for each of the above mentioned operating mediums and can be used in a coupling device for different medical devices which require different selected operating mediums.

Thus, the coupling links for the pair of coupling halves for a given operating medium have the same dimensions on all handpieces and are positioned in the exact same spatial point of the pattern. Therefore, coupling links for spray air and spray water for a coupling half attached to a turbine handpiece are identically constructed with regard to their dimensions and positions in the coupling half as for example the same coupling links in a coupling half which is utilized in the case of a spray handpiece. In a similar manner, the coacting coupling links for interconnecting a light conductor on the coupling halves used with turbine handpieces will be arranged in the same exact position as in the coupling halves for an illumination handpiece.

The proposed arrangement for the coacting coupling links in the pair of coupling halves will be in accordance with a layout or plan which takes into consideration all of the possible operating mediums, which might be utilized with each of the dental handpieces so that it is possible to use one type of coupling device for connecting any one of the different types of dental handpieces to its respective supply tube. If the supply tube also includes feed lines for all of the possible operating mediums which may be required for each of the different types of handpieces and if all of the coupling links on the coupling half attached to the supply tube are connected to the respective feed lines, it is possible that one single supply tube can be utilized with a plurality of different types of handpieces. In such an instance, the coupling half attached to each of the dental handpieces will be provided with dummy coupling links for each of the operating mediums which are not required for that particular handpiece so that when the particular handpiece is interconnected through its coupling half to the coupling half on the supply tube, the operating mediums which are not required for that handpiece are not connected thereto.

DESCRIPTION OF THE PREFERRED EMBODIMENT

Figure 1:
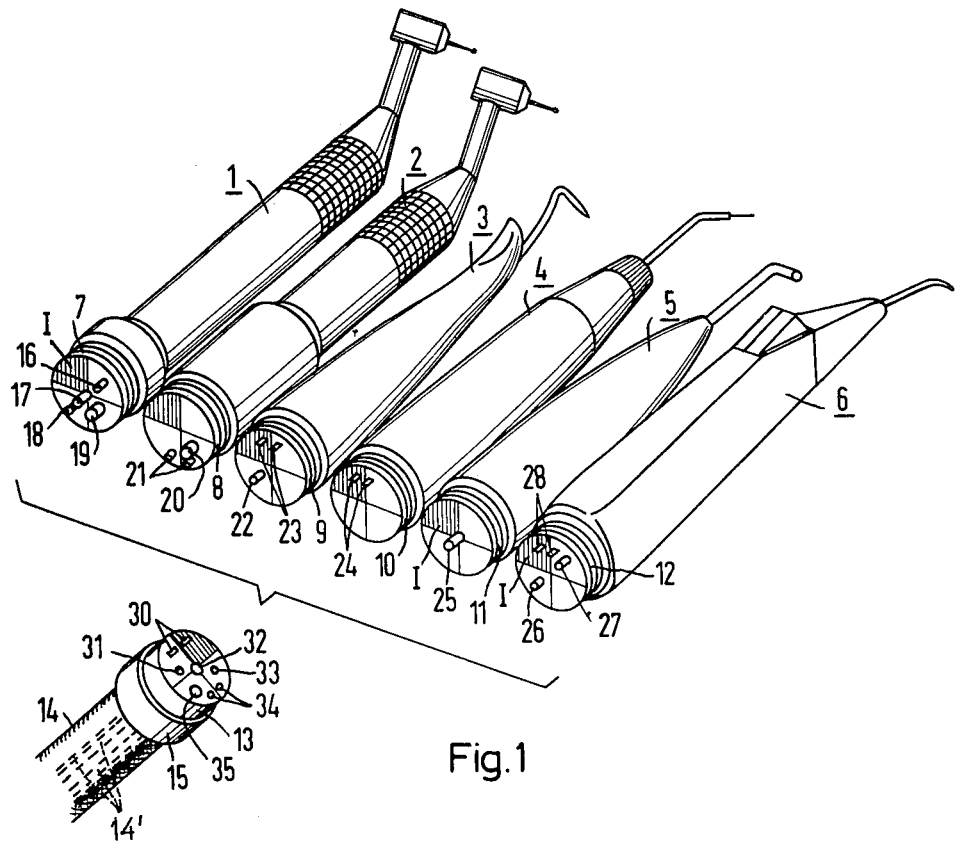
FIG. 1 is a perspective view illustrating the coupling device in accordance with the present invention which can be utilized to couple any one of six different types of dental handpieces to the supply tube.

The principles of the present invention are particularly useful in a coupling device for interconnecting the supply tube to a medical device such as one of the six dental handpieces illustrated in FIG. 1 which include a turbine handpiece 1, a micromotor handpiece 2, an ultrasonic tartar remover handpiece 3, a HF-electrosurgical handpiece 4, an illumination handpiece 5 and a spray handpiece 6. Each of the handpieces 1-6 is provided with a coupling half 7-12, respectively, which may be detachably connected to the respective handpiece or permanently attached thereto.

As illustrated, each of the halves 7-12 have different arrangements of coupling links which are illustrated as male or plug-type links which are in communication with respective conduits in the handpieces. The coupling links of the halves 7-12 are received in socket-type coupling links provided in a coupling half 13 which is detachably or permanently connected to a supply tube 14 which has feed lines 14' for each of the operating mediums. To hold any one of the coupling halves 7-12 in a coupling arrangement with the coupling half 13, a connecting means comprising a connecting nut 15 which is threadably received on the selected coupling half 7-12 is provided.

As mentioned hereinbefore, each of the coupling halves 7-12 is provided with coupling links. The coupling half 7 which is either permanently or detachably connected to the turbine handpiece 1 is provided with a coupling link 16 for a gas such as auxiliary air (spray air), coupling link 17 for a light conductor, coupling link 18 for cooling water, and coupling link 19 for a gas such as propulsion air. Each of these coupling links 16-19 are connected to appropriate conduits for the different mediums which conduits are provided in the handpiece 1.

The micromotor handpiece 2, which includes a miniature electric motor for providing a drive means to rotate the drill or burr, is connected to a coupling half 8 which has a prong-shaped coupling link 20 for a high volume gas flow such as propulsion air, and a pair of coupling links 21 for supplying electrical power or current to the motor. The ultrasonic handpiece 3 has the coupling half 9 which is provided with a tubular coupling link 22 in the shape of a plug or prong for receiving cooling or spray water and a pair of coupling links 23 for receiving the high frequency drive current for the ultrasonic device. The electrosurgical handpiece 4 has the coupling half 10 which is provided with a pair of coupling links 24 in the form of prongs for supplying the high frequency electrical energy necessary for the operation of electrosurgical device. The illumination handpiece 5 has the coupling half 11 which has a coupling link 25 which is an optical coupling link for a light conductor. The spray handpiece 6 has the coupling half 12 which is provided with a tubular coupling link 27 for auxiliary air and a coupling link 26 for water and is also provided with two electrical coupling links 28. Each of the above coupling links are in the shape of prongs. Those links utilized for transmitting fluids such as water or air are hollow tubular links.

The coupling half 13 is attached to the supply tube 14 and is provided with coacting coupling links for the above mentioned coupling links attached to the various halves 7 through 12. Each of these coupling links is illustrated as being in the form of a socket or a female coupling link and comprise a pair of sockets 30 which are positioned to receive the prongs 23, 24 or 28 on the halves 9, 10 and 12, respectively. In addition, the half 13 has a coupling link that is formed by a socket 31 for auxiliary air, a coupling link or socket 32 for a light conductor, a socket 33 for cooling or spray water, a socket 35 for main propulsion air and a pair of sockets 34 for electrical current to coact with the coupling links 21 for the coupling half 8 on the micromotor handpiece 2. Thus, the coupling half 13 can be used with any one of the coupling halves 7-12. It should be noted that the coacting sets of coupling links for each of the different fluids, such as propulsion air, auxiliary air and water, are provided with appropriate seals to ensure a fluid tight connection.

Figure 2:
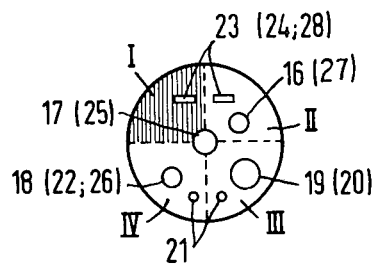
FIG. 2 is a pattern for the arrangement of the various coupling links on a coupling half which would be attached to one of the dental handpieces.

To enable using the coupling half 13 with any of the coupling halves 7-12, the various coupling links are positioned on each of the coupling halves 7-12 in a precise special spatial location in accordance with a layout or pattern which is best illustrated in FIG. 2. In the layput of FIG. 2, the end face of each coupling half is divided in four quadrants I, II, III and IV. Thus, the coupling links 16 and 27 for cooling or spray air are positioned in the exact same spatial position in quadrant II and the cooling water coupling links 18, 22 and 26 are at the exact same position in quadrant IV. The propulsion air coupling links 19 and 20 are located in quadrant III and the coupling links 17 and 25 for the light conductor are located on the central axis of the half which is the most advantageous position for the location of the light conductor coupling. As illustrated, the links 21 for applying electrical power of the micromotor are located in one position and the links such as 23 and 24 which will apply a different voltage or frequency for electrical current are in another portion of the layout at the same position.

In the layout of FIG. 2, coacting coupling links for only two different types of electrical connections are provided. If more than two types of electrical operating mediums are required an additional set of coacting electrical coupling links can be provided. It is also possible to use the same set of coacting electrical coupling links to transfer more than one type of electrical operating medium by providing means to separate the different electrical operating mediums. For example, if the opposite ends of the feed lines of the supply tube are connected to a device which enables selectively connecting different electrical operating mediums to the feed lines, the feed lines can be used to transfer different electrical mediums at different times.

In the layout illustrated in FIG. 2, the end of the coupling half is divided in four quadrants with the various coupling links being disposed in specific quandrants. It should be noted that the use of four quadrants is not necessary and that the only requirement is that the spatial position for each set of coacting coupling links, such as the propulsion air coupling link 19 and 20, be in the exact same position in each pattern or layout. It is also noted that the layout of the various coupling links for a medical device will be determined by the maximum possible types of operating mediums that will be required for the various medical devices.

In FIG. 1, each of the coupling halves 7–12 is provided with only those coupling links which are necessary for communicating the specific operating medium or mediums which are required by the respective handpiece. However, the coupling half 13 which is attached to the supply tube is provided with the mating coupling links for all possible combinations. It is also possible to reduce the number of different types of coupling halves by providing a universal coupling half having all of the coupling links in accordance with the layout in FIG. 2. In such an instance, the coupling links, which are not required for the particular handpiece, are dummy links so that the operating medium will not be transferred or interconnected through the coacting coupling halves. It should be noted that while the coupling half 13 which is attached to the supply tube is indicated as having female or socket-type coupling links, it could be provided with the projecting or male-type coupling links with the sockets being provided on the coupling halves attached directly to the handpieces. As pointed out hereinabove, if all of the coupling links 31–35 are connected to respective feed lines 14', then the single supply tube 14 can be utilized for any one of the handpieces such as 1–6. If the coupling halves attached to the handpieces 1–6 are provided with dummy coupling links, which may be electrical prongs that are not connected to any electrical circuit in the handpiece or a tubular fluid transmission link, which has been sealed in some manner such as by plugging, the coupling halves in accordance with the present invention will enable a high flexibility in the selection of a handpiece for use with a given supply tube. It should be noted that each of the feed lines 14' in the supply tube such as 14 will extend to an operating cabinet which will have appropriate controls, such as valves for the fluid mediums and switches for the electrical mediums which will de-energize the respective feed lines during the connecting and disconnecting of the coupling halves.

Another use of the coupling halves such as illustrated in FIGS. 1 and 2, is to provide a standardized coupling half for each of the handpieces and for the supply lines. However, the supply tube 14 for a certain type handpiece will only have feed lines 14' for the operating mediums required by that type of handpiece and thus only certain coupling links of the half 13 will be connected to a feed line and be alive and other links will be dead or dummy links. Thus, if the supply tube 14 was to be used only with turbine handpieces 1, only the coupling lines 33 for water, 32 for light, 31 for auxiliary air and 35 for propulsion air would be connected to feed lines. The remaining links such as 34 and 30 would not be connected to the feed lines 14' and would thus be a dummy socket. While this will reduce the cost of the installation, it will also reduce the flexibility of using the supply tube with any other device that would require the various electrical operating means such as the micromotor handpice 2, the ultrasonic handpiece 3 and the electrosurgical handpiece 4. Thus, such an arrangement would reduce the flexibility of using the particular supply tube by reducing the number of types of handpieces that may be used therewith.

Figure 3:
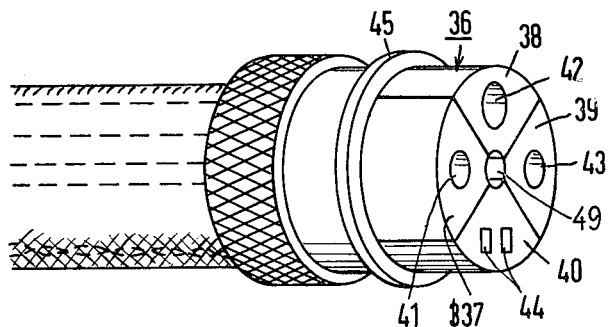
FIG. 3 is a perspective view of a sample embodiment of a coupling half attached to a supply tube in accordance with the present invention.
Figure 4:
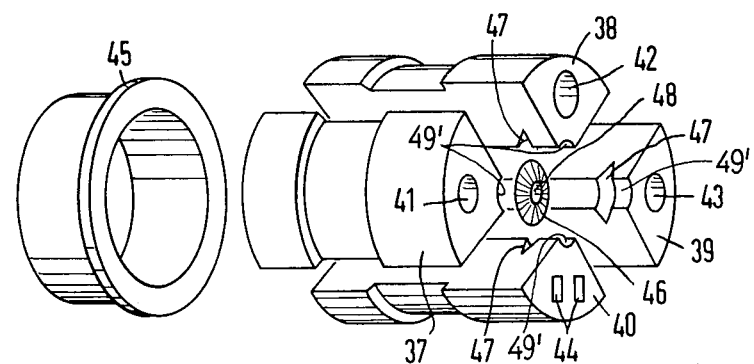
FIG. 4 is an exploded perspective view of a coupling half illustrated in FIG. 3.

In the embodiment of the coupling halves illustrated in FIG. 1, the halves such as 7–12 and 13 are each a solid member. However, either the two coupling halves or only one can be formed of several individual elements such as illustrated in FIGS. 3 and 4. In this embodiment of the coupling device, a coupling half generally indicated at 36 is composed of four coupling elements or segments 37–40, which have a sector shape cross section and each coupling element contains a coupling link such as sockets 41–44, which will be associated with a specific type of operating medium. The four coupling elements are held together by a ring 45.

As shown in FIG. 4, the coupling half 36 includes a disk 46. The segments 37–40 are each provided with a notch 47 which is engaged on the disk 46 when the four segments are assembled as illustrated in FIG. 3. The disk 46 will prevent axial shifting of any of the segments and is provided with an aperture 48 which is aligned with a channel 49 at the center axis of the coupling half 36. As illustrated, each segment 37–40 has an axially extending groove 49' which grooves 49' coact to form the channel 49 which can be utilized for receiving a light conductor and for forming one of the coupling links for a light conductor. With this type of construction using a plurality of elements that are assembled together, it is very advantageous if the outer dimensions of each of the elements 37–40 are the same so that the elements are interchangeable. Thus, a coupling half can be formed to provide the necessary operating mediums by selecting the various segments that would be required for forming a coupling link for transmitting each of the desired operating mediums. If necessary, socalled dummy sectors or elements which are not provided with the desired coupling link can be substituted when desired. It should be noted that while only the coupling half attached to the supply tube is illustrated, the coupling halves that are attached to the various handpieces can also be formed in the same manner.

Figure 5:
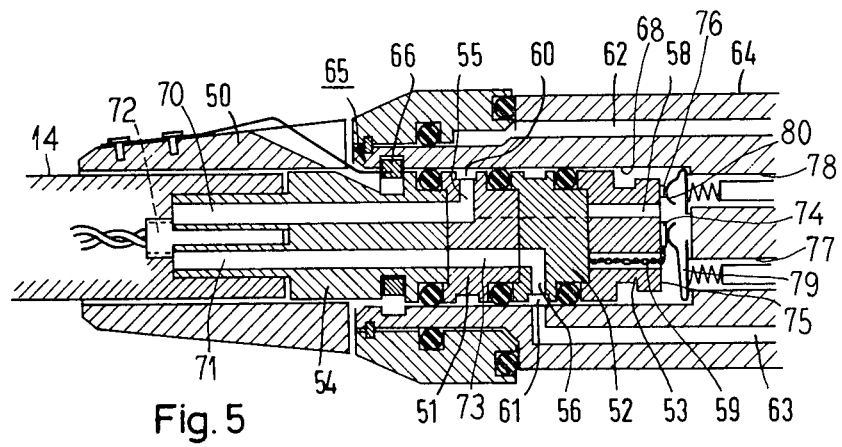
FIG. 5 is a longitudinal cross-sectional view of an embodiment of a coupling half of a coupling device in accordance with the present invention.

In an embodiment illustrated in FIG. 5, the coupling halves of the coupling device have been constructed to form a rotational coupling. This coupling device includes a coupling half 50, which is illustrated as being attached to a supply tube 14, and a coupling half 64 which has a socket 68 and is attached to a handpiece. The half 50 is essentially formed of several disk-shaped elements 51, 52 and 53 which are axially mounted on a base member or body 54 of the coupling half 50. In particular, the disk-shaped elements are preferable cemented to one another to form a plug that is received in the socket 68. Each of the elements 51, 52 and 53 advantageously have identical disk thickness so that the illustrated elements may be interchanged in two axial positions on the plug or be replaced by similar elements which are constructed to communicate different operating mediums without changing the axial length of the plug position.

The base member 54 is provided with a plurality of axially extending channels such as 70, 71 and 72. The next adjacent portion 51 has an axial extending channel in communication with the channel 70 of the member 54 and extends into a radial channel 55 that has a port opening into a ring channel 60. In addition, for each of the remaining channels 71 and 72 of the base member 54, the element 51 has longitudinal channels (only channel 73 is shown) which extends axially through the element and are in separate communication with the other axial channels of the member 52. In a similar manner, the element 52 has a radial channel 56 having an axial extending portion in communication with the channel 73 of the element 51. The radial channel 56 opens in a peripheral port in communication with a ring groove 61. The element 52 also has an axially extending channel (not illustrated) for each channel of member 54 that is not connected to either channel 55 or 56.

As illustrated, the element 53 has channels 58 and 59 which extend axially through the element which, for the purpose of illustration, has been rotated approximately 90° on the axis of the plug from its position relative to the other elements 51 and 52. The channel 59 is in communication with axially extending channels in the elements 52, 51 (not illustrated) and channel 72 of member 54 and channel 58 is in communication with axial extending channels in elements 52, 51 and member 54 which channels are not illustrated. Through these channels, the channels 58 and 59 are in communication to convey a high volume medium such as a high volume flow of air from the tube 14 through the coupling half 50. By utilizing axially extending channels for the high volume of air, a minimum amount of restriction to the flow of air is imposed. In addition to transferring a high volume of air, channels such as 59 may contain electrical leads for supplying electrical current to a contact 74 on an end face 75 of the element 53. Another contact 76 on the end face 75 is also supplied by electrical current by a wire (not illustrated).

To isolate the various fluids such as fluid in the ring channel 60 from the fluid in the ring channel 61, each of the elements such as 51, 52 and 53 as well as the member 54 are provided with coacting shoulders and grooves so that when the elements are cemented together, the coacting shoulders and grooves entrap a plurality of axially spaced sealing means such as O-rings. These sealing rings coact with an inner cylindrical surface of a socket 68 of the other coupling half 64 to isolate the fluids in the various ring channels and fluids that are released through the passages 58 and 59.

The coupling half 64 is provided with various conduits such as 62, 63, 77 and 78. The conduit 63 extends axially to a radial portion which opens in a port in communication with the ring channel 61. In a similar manner, the channel 62 also is in communication with the ring channel 60 by a radial extending port which is not illustrated. The channels 77 and 78 will receive the operating fluid being discharged through channels 58 and 59. In addition, these channels contain electrical circuits having spring contacts 79 and 80 which respectively engage or slide on the contacts 74 and 76.

To hold the two coupling elements together, a mechanical arresting device or locking means generally indicated at 65 is provided. As illustrated, the locking means 65 includes a ring 66 which extends between a circumferential groove in the base member 54 and in a circumferential groove in a claw-like constructed end piece of the coupling half 64. Due to the spring mounting of the ring 66 in one of these grooves, the ring 66 is engaged in both grooves to lock the halves 50 and 64 together but allows relative axial rotation between the halves.

When the coupling device such as illustrated in FIG. 5 is coupling an operating medium such as a fluid having a high volume flow, it is desirable that the channels to the coupling links extend either on the axis of the coupling halves or parallel to the axis to reduce the probability of interferrence with the flow through the coupling device. Other fluid operating mediums, such as water and auxiliary air, preferably utilize coacting coupling links which have radially opening ports interconnected by a ring channel and isolated by seals. If electrical current or voltages are included in the operating medium, the coacting coupling links are arranged preferably on the front face 75 or on a peripheral region of the plug portion adjacent the front face 75 so that the respective coacting link such as 79 and 80 may be engaged therewith regardless of relative axial rotation of the plug in the socket.

As described hereinabove, with regard to the coupling device of the embodiment illustrated in FIG. 5, the axial spacing of the various coupling links from the end of the plug of the coupling half 50 has an advantage that when the electrical connections are adjacent the end face 75 of the plug, auxiliary air is axially spaced inward from the end and the coacting links for water are at an axial position which has the greatest axial distance from the electrical links. Therefore, if leakage should occur, a minimum of disruption of the functions will arise and it is very desirable to prevent any contact of the water with electrical contacts of the rotational coupling. Thus, even if leakage should occur through the seals adjacent the channel ring 60, additional seals must be passed before the water will come into contact with the electrical contacts such as 75 and 78. If the coupling for a light conductor is provided, it is preferably formed by coupling links that are located on the central axis of the two halves 50 and 64.

As mentioned hereinabove with regard to the one-piece coupling halves illustrated in FIGS. 1 and 2, coupling half attached to the supply tube may be provided with a coupling link for each of the various different operating mediums. The other half of the structure illustrated in FIGS. 3 and 4 or a rotational coupling of FIG. 5 will have dummy coupling links such as provided by closed ports so that operating means in the supply tube which is connected to the coupling links of the coupling half 50 are not connected through the coupling half 64 to the handpiece. Thus, different handpieces having different requirements for operating means can be utilized with a single supply tube having the coupling half 50.

As mentioned above, it is also possible that the coupling half 50 which is provided with coupling links for each of the operating means is only connected to a supply tube which has only feed lines for a specific number of operating means so that the certain coupling links are not connected to a feed line and therefore become dead or dummy coupling links. In either case, the standardization of the various number of coupling halves will reduce the number of different parts that will be necessary and therefore reduces the expenses for designing, manufacturing and storing a plurality of different types of parts.

Although various minor modifications might be suggested by those versed in the art, it should be understood that I wish to employ within the scope of the patent granted hereon, all such modifications as reasonably and properly come within the scope of my contribution to the art.

I claim:

1. In a coupling device for detachably connecting a medical device, which requires at least one operating medium, in particular a dental tool, including a turbine handpiece having a spray air conduit, a water conduit, and a main gas propulsion conduit; a micromotor handpiece having a high volume gas flow conduit and a pair of electrical conductors; an ultrasonic handpiece having a spray water conduit and a pair of conductors for the high frequency drive current; an electrical surgical handpiece having a pair of high frequency energy conductors; an illumination handpiece having a light conductor; and a spray handpiece having a spray air conductor and spray water conduit, to a supply tube containing feed lines for at least one of the operating mediums, said coupling device including a pair of coupling halves with a first coupling half connected to the medical device and having a first coupling link for each of the conduits and a second coupling half connected to the supply tube and having a second coupling link for each feed line, and means interconnecting the pair of coupling halves with the first and second coupling links coacting to interconnect the feed line of the supply tube to the respective conduit of the medical device, the improvement comprising the first and second coupling links for each operating medium being provided on said first and second halves in a specific spatial position in accordance with a pattern so that the second coupling half can be selectively connected to a feed line for each of the above mentioned operating mediums and can be used in a coupling device for different medical devices which require different selected operating mediums.

2. In a coupling device according to claim 1, wherein each of said first and second coupling links is a coacting plug and socket.

3. In a coupling device according to claim 1, wherein said first and second coacting coupling links are disposed on respective flat surfaces of the coupling halves which flat surfaces are in a facing relationship when the pair of coupling halves are held together by the means for interconnecting.

4. In a coupling device according to claim 1, wherein the first and second coupling links for interconnecting light from the first to the second coupling halves are disposed on a center axis of the coupling halves.

5. In a coupling device according to claim 1, wherein at least one of the pair of coupling halves comprises a plurality of uniformly constructed individual elements, each element containing at least one coupling link for the one half.

6. In a coupling device according to claim 5, wherein the individual elements have essentially a sector-shaped cross section and are assembled around the axis of the one coupling half to form said coupling half.

7. In a coupling device according to claim 6, wherein said sectors cooperate to hold a light conductor on the center axis and wherein the coacting coupling links for interconnecting light are disposed on the center axis of each coupling half.

8. In a coupling device according to claim 5, wherein each of said individual elements has a disk-shape and are arranged axially one behind the other in the coupling half.

9. In a coupling device according to claim 8, wherein one of the pair of coupling halves has a socket and the other of said pair of coupling halves has a plug portion telescopically received in the socket with relative rotation therebetween to form a rotational coupling.

10. In a coupling device according to claim 9, wherein the plug portion has an end face, wherein coacting coupling links for each of the gases and water are coacting ports with means for isolating a fluid of the one set of coacting ports from the other sets of coacting ports, and wherein the spatial position of each coupling link has the links for the light, electrical current and propulsion gas disposed on the end face of the projecting portion of the ports for the auxiliary gas and water being axially spaced from the end face with the water ports being the furthest from the end face.

11. In a coupling device according to claim 9, wherein each of said pair of coupling halves has an axial extending channel for conveying a high volume flow fluid through the coupling device.

12. In a coupling device according to claim 9, wherein the coacting connecting links for the auxiliary gas and the water each comprise a set of coacting ports, each port being in communication with radial extending channel in the respective coupling halves, one of each set of ports being in communication with a ring channel with the ring channel of one set being axially spaced from the ring channel of the other set.

13. In a coupling device according to claim 9, wherein the coupling links for electrical current are disposed adjacent an end face of the plug portion and a bottom of the socket and comprise a spring contact on one half engaging a metal contact on the other half to enable relative rotation between the halves.

14. In a coupling device according to claim 9, wherein the means for interconnecting the pair of halves together comprises aligned radial grooves on the plug portion and the wall of the socket, and a locking element received in one of said grooves and biased into engagement in the other groove.

* * * * *